United States Patent
Xue et al.

(10) Patent No.: US 12,043,617 B2
(45) Date of Patent: Jul. 23, 2024

(54) 4-(N-METHYL) AMINOPIPERIDINE MYRICETIN DERIVATIVE CONTAINING DITHIOCARBAMATE, PREPARATION METHOD AND APPLICATION

(71) Applicant: Guizhou University, Guiyang (CN)

(72) Inventors: Wei Xue, Guiyang (CN); Shichun Jiang, Guiyang (CN); Ziyou Huai, Guiyang (CN); Xu Tang, Guiyang (CN); Yinjiu Huang, Guiyang (CN); Liwei Liu, Guiyang (CN); Mei Chen, Guiyang (CN); Jun He, Guiyang (CN); Shijun Su, Guiyang (CN)

(73) Assignee: Guizhou University, Guiyang (CN)

( * ) Notice: Subject to any disclaimer, the term of this patent is extended or adjusted under 35 U.S.C. 154(b) by 95 days.

(21) Appl. No.: 17/043,508

(22) PCT Filed: Dec. 5, 2019

(86) PCT No.: PCT/CN2019/123150
§ 371 (c)(1),
(2) Date: Sep. 29, 2020

(87) PCT Pub. No.: WO2020/253140
PCT Pub. Date: Dec. 24, 2020

(65) Prior Publication Data
US 2023/0219935 A1    Jul. 13, 2023

(51) Int. Cl.
*C07D 405/12*    (2006.01)
(52) U.S. Cl.
CPC .................. *C07D 405/12* (2013.01)

(58) Field of Classification Search
CPC .................................................... C07D 405/12
See application file for complete search history.

(56) References Cited

FOREIGN PATENT DOCUMENTS

| CN | 103804335 | | 5/2014 | |
| CN | 103804335 | * | 5/2016 | ........... C07D 311/30 |
| CN | 107021945 | | 8/2017 | |
| CN | 110183429 | | 8/2019 | |

OTHER PUBLICATIONS

Huang, Wei, Synthesis and Antitumor Activity of Novel Dithiocarbamate Substituted Chromones, European Journal of Medicinal Chemistry, Apr. 9, 2009.

* cited by examiner

*Primary Examiner* — Nizal S Chandrakumar

(57) ABSTRACT

The invention discloses a 4-(N-methyl) aminopiperidine myricetin derivative containing dithiocarbamate, and its preparation method and application, whose structural general formula is shown as follows: wherein R is substituted phenyl and substituted aromatic heterocyclic group; n is the number of carbons in the carbon chain, which are 2, 3, 4 and 5 respectively; the substitute phenyl group is an alkyl group containing C1-6, alkoxy group containing C1-6, nitro group, halogen atom or hydrogen atom in ortho-, meta- and para-position on that benzene ring; the aromatic heterocyclic group is thienyl, furyl, pyrrolyl and pyridyl groups; the substituents on the substituted aromatic heterocycle are o-, m-, and p-containing C1-6 alkyl, C1-6 alkoxy, nitro, halogen, and hydrogen atoms. The invention has better inhibitory activity on cancer cells.

5 Claims, No Drawings

4-(N-METHYL) AMINOPIPERIDINE MYRICETIN DERIVATIVE CONTAINING DITHIOCARBAMATE, PREPARATION METHOD AND APPLICATION

FIELD OF THE INVENTION

The invention relates to the technical field of chemical industry, in particular to a 4-(N-methyl) aminopiperidine myricetin derivative containing dithiocarbamate, a preparation method of the 4-(N-methyl) aminopiperidine myricetin derivative containing dithiocarbamate, and an application of the 4-(N-methyl) aminopiperidine myricetin derivative containing dithiocarbamate in inhibiting tumor cells.

BACKGROUND OF THE INVENTION

Natural products are also called secondary metabolites, and most of them, such as flavonoids, phenols, alkaloids, terpenes and polysaccharides, have insecticidal, antibacterial and antitumor activities. Natural products have a wide variety of chemical components, novel structures, high efficiency, low toxicity and little toxicity to human beings and the environment (Li Kun, Yang Yifang, Chinese herbal medicine, 2009, 39, 1417-1424.), which play an important role in the discovery of new drugs and lead compounds. Finding highly active compounds from natural products, modifying them and green synthesis to obtain new drugs with high activity and low toxicity have become one of the hot topics in research and development of new drugs.

Myricetin is also called myricetin ketone, which belongs to flavonol compounds and widely exists in various plants with rich sources. In 2000, He Guixia et al. (He Guixia, Pei Gang, et al. Chinese Journal of Ethnic Medicine, 2000, 6, 40-41.) isolated this compound from the stem of Ampelopsis grossedentata. Pharmacological studies show that myricetin has biological activities such as anti-tumor, antibacterial, antiviral, antioxidant and anti-inflammatory activities, and has certain research and application value.

In 2011, Zhang et al. (Zhang Lijing, Wang Mingqian, Li shizhen medicine and materia *medica* research, 2011, 1, 31.) used mice abdominal cavity infection model to observe the protective effect of myricetin on the mice infected by *Staphylococcus aureus* (*S. aureus*), *Streptococcus pneumonia* (*S. pneumonia*), type A hemolytic *streptococcus* (A Stretococus); the preventive effects of myricetin on ear swelling induced by xylene and granuloma induced by agar in rats are observed. The results show that myricetin has good antibacterial and anti-inflammatory activities in mice.

In 2014, Zhao et al. (Zhao Hongju. Study on Synthesis and Bioactivity of Myricetin Derivatives [D]. Guizhou University, 2014) reported a series of heterocyclic alkyl myricetin derivatives. MTT method is used to test the in vitro proliferation inhibitory activity of the synthesized compounds on breast cancer cell MDA-MB-231. Among them, at the concentration of 1 µmol/L, the inhibitory activity of some compounds is higher than that of the control drug gefitinib (9. 73±8.04%).

In 2015, Xue et al. (Xue, W, Song, B. A., Zhao, H. J. Eur. J. Med. Chem., 2015, 97, 155-163.) reported a series of myricetin derivatives containing acylhydrazones. In vitro proliferation inhibitory activity of the synthesized compounds on human breast cancer cell MDA-MB-231 is tested by MTT method. The results show that myricetin acylhydrazone derivatives have good inhibitory rate on human breast cancer cell MDA-MB-231.

In 2017, Xiao et al. (Xiao Wei, Ruan Xianghui, Li Qin, et al. Chemical Journal of Chinese Universties, 2017, 38, 35-40.) reported a series of amide myricetin derivatives, and tested their inhibitory activities against *Xanthomonas oryzae* pv, *oryzae, Xanthomonas campestris* pv, *citri* and *Ralstonia solanacearum*. The test results showed that these compounds had certain inhibitory activities against 3 bacteria tested.

In 2017, Zhong et al. (Zhong, X. M., Wang, X. B., Chen, L. J., et al. Chem. Cent. J., 2017, 106.) synthesized a series of compounds containing 1,3,4-thiadiazole structure. The activity of the synthesized compounds against tobacco mosaic virus (TMV) is determined by half leaf blight method. Preliminary test results show that at the concentration of 500 µg/mL, the EC50 value of some compounds to TMV is better than that of ningnanmycin in terms of therapeutic activity. At the concentration of 100 µg/mL, the EC50 value of some compounds on bacterial leaf blight of rice is better than that of the commercial control drug thiamethoxam copper.

In 2018, Ruan et al. (Ruan, X. H., Zhang, C., Jiang, S. C., et al. molecules, 2018, 23, 3132.) designed and synthesized a series of myricetin derivatives containing amide, thioether and 1,3,4-thiadiazole groups, and evaluated their antibacterial activities. The bioassay results showed that the compound had certain inhibitory activity on *Xanthomonas oryzae* pv. *oryzae, Xanthomonas citri* and *Ralstonia solanacearum*.

In summary, myricetin has good antibacterial, antiviral and antitumor activities. Our research group has studied a series of myricetin derivatives and tested their biological activity. It is found that some myricetin derivatives have certain inhibitory activity on human cancer cells.

But the activity is not high and the application is not strong.

SUMMARY OF THE INVENTION

The purpose of the present invention is to provide a 4-(N-methyl) aminopiperidine myricetin derivative containing dithiocarbamate which has better inhibitory activity on cancer cells and overcomes the above disadvantages.

Another object of the present invention is to provide a preparation method of the 4-(N-methyl) aminopiperidine myricetin derivative containing dithiocarbamate.

Another object of the present invention is to provide the application of the 4-(N-methyl) aminopiperidine myricetin derivative containing dithiocarbamate in inhibiting tumor cells.

The structural general formula of the 4-(N-methyl) aminopiperidine myricetin derivative containing dithiocarbamate is as follows:

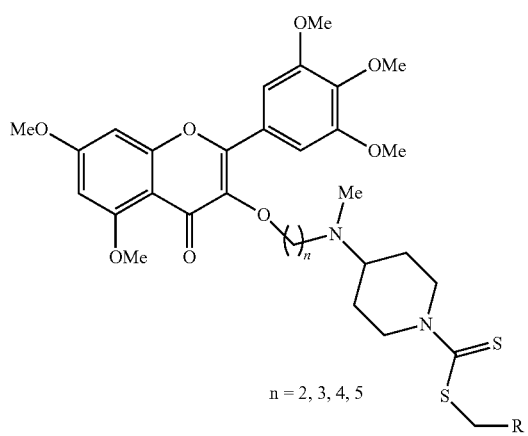

n = 2, 3, 4, 5

Wherein R is substituted phenyl and substituted aromatic heterocyclic group; n is the number of carbon in the carbon chain and can be 2, 3, 4 or 5. The substituted phenyl group is an alkyl group containing C1-6 on ortho-, meta- and para-position of the benzene ring, an alkoxy group containing C1-6, nitro, halogen atom, hydrogen atom, etc., the aromatic heterocyclic group is thienyl, furyl, pyrrolyl, pyridyl, etc., and the substituent on the substituted aromatic heterocyclic ring is an alkyl group containing C1-6 on ortho-, meta- and para-position, an alkoxy group containing C1-6, nitro, halogen atom, hydrogen atom, etc.

In this invention, the preparation method of the 4-(N-methyl) aminopiperidine myricetin derivative containing dithiocarbamate comprises the following specific steps:

(1) 3-hydroxy-3', 4',5',5,7-pentamethoxy myricetin (intermediate a) is prepared from myricetin and methyl iodide as raw materials and crystalline potassium carbonate as catalyst under acidic conditions.

(2) 3-bromo-5,7-dimethoxy-2-(3,4,5-trimethoxyphenyl)-4H-chromene-4-one (intermediate b) is prepared from intermediate a and dibromoalkanes with different chain lengths using potassium carbonate as catalyst and N,N-dimethylformamide (DMF) as solvent, as follows:

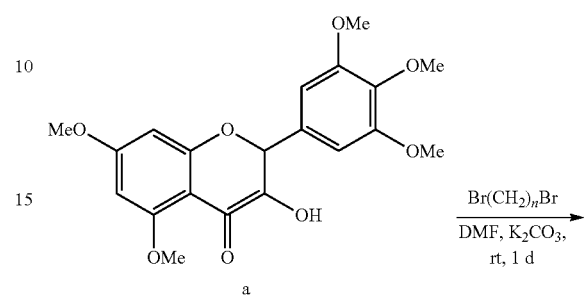

(3) Using intermediate b and 4-(N-methyl) amino-N-Boc piperidine as raw materials, potassium carbonate as catalyst and acetonitrile as solvent, 3-(4-(N-methyl) amino-N-Boc piperidine)-5,7-dimethoxy-2-(3,4,5-trimethoxyphenyl)-4H-chromene-4-one (intermediate c) is prepared under reflux and stirring at 80° C.

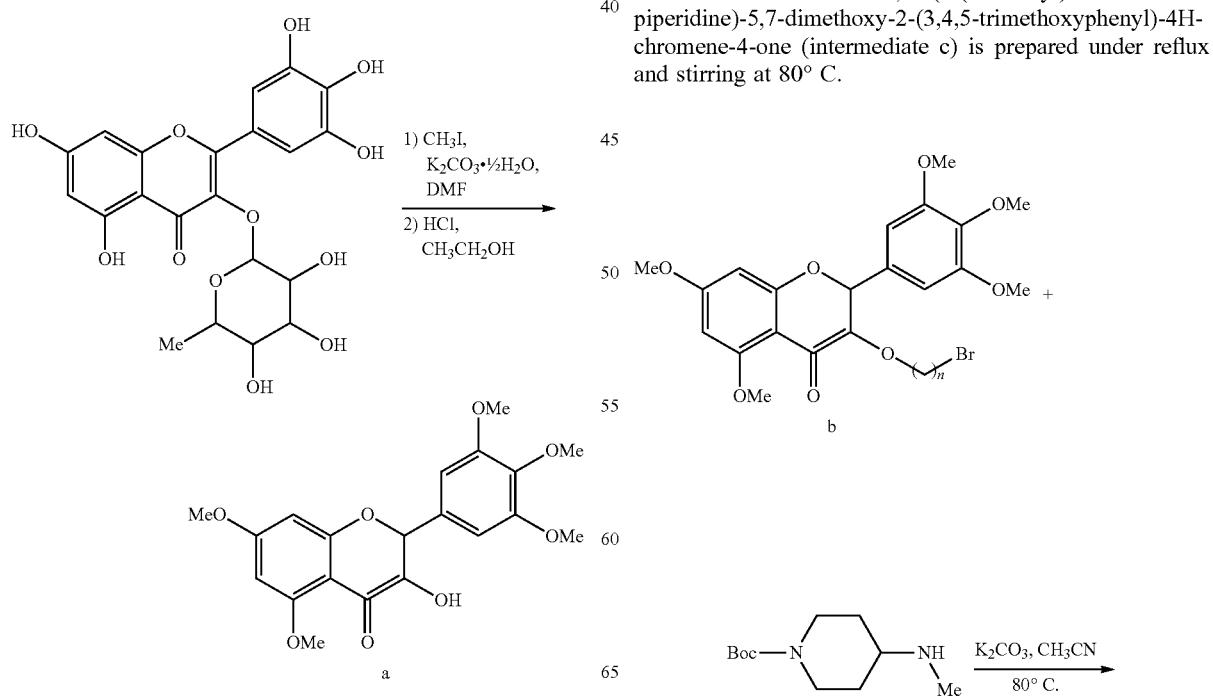

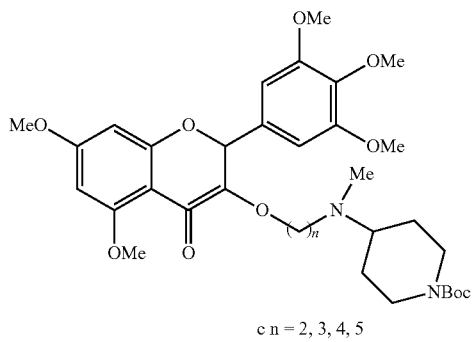

c n = 2, 3, 4, 5

(4) Taking intermediate c as raw material, Boc protection is removed by HCl to obtain hydrochloride (intermediate d) of 3-(4-(N-methyl) aminopiperidine)-5,7-dimethoxy-2-(3,4,5-trimethoxyphenyl)-4H-chromene-4-one, as shown below:

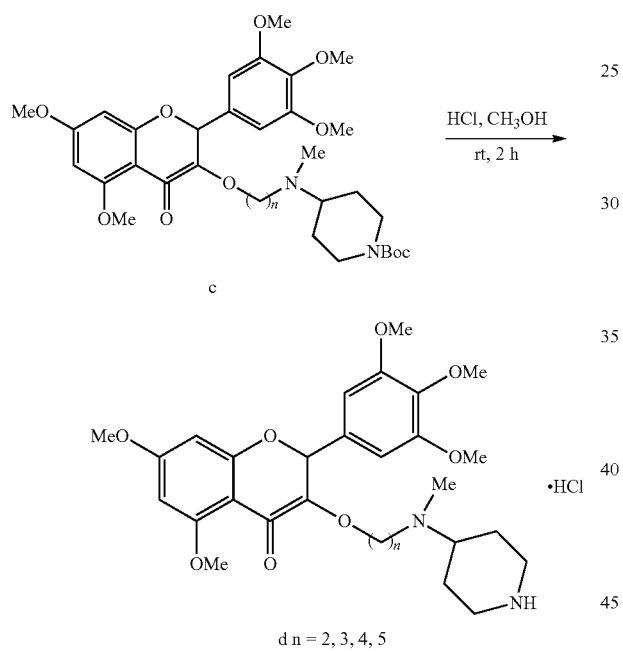

d n = 2, 3, 4, 5

(5) 4-(N-methyl) aminopiperidine myricetin derivative containing dithiocarbamate (target compound A) is prepared by taking intermediate d, carbon disulfide and benzyl chloride as raw materials, potassium carbonate as catalyst and acetonitrile as solvent, as shown below.

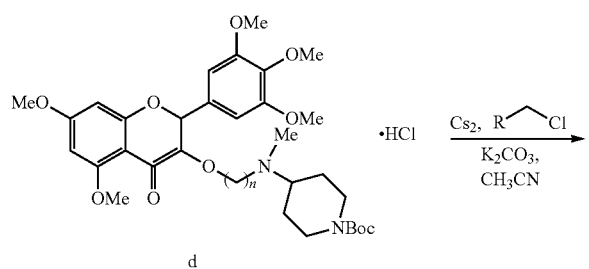

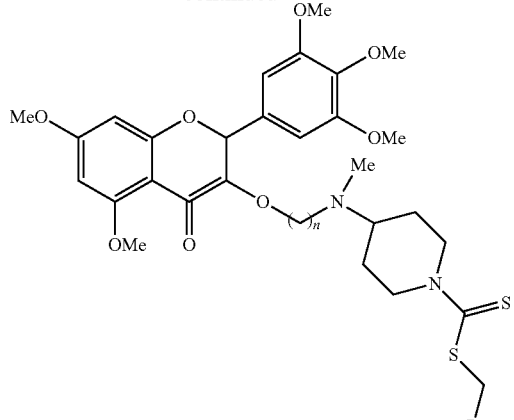

A n = 2, 3, 4, 5

The application of 4-(N-methyl) aminopiperidine myricetin derivative containing dithiocarbamate in preparing medicine for inhibiting cancer cells is disclosed.

Compared with the prior art, the invention has obvious beneficial effects. From the above technical scheme, the invention introduces 4-(N-methyl) aminopiperidine molecules containing dithiocarbamate with biological activity into the structure of myricetin to synthesize a series of 4-(N-methyl) aminopiperidine myricetin derivatives containing dithiocarbamate, and tests the inhibitory activity on cancer cells by MTT method, indicating that the 4-(N-methyl) aminopiperidine myricetin derivatives containing dithiocarbamate have better inhibitory activity on cancer cells.

DETAILED DESCRIPTION OF THE INVENTION

Embodiment 1

The preparation method of 4-chlorobenzyl 4-((3-((5,7-dimethoxy-4-oxo-2-(3,4,5-trimethoxyphenyl)-4H-chromene-3-yl)oxy)propyl)(methyl)amino)piperidine-1-dithiocarboxylic acid (target compound A1) comprises the following steps:

(1) Preparation of 3-hydroxy-3', 4', 5', 5,7-hentamethoxy-myricetin (intermediate a): 4.64 g myricetin (10 mmol), 22.09 g K2CO3·½H2O (16 mmol) and 120 mLDMF are added into a 250 mL round-bottom flask in turn. after stirring for 0.5-1 h at room temperature, 7.50 mL iodomethane (120 mmol) is slowly added dropwise, stirring at room temperature for 48 h, and TLC followed the reaction (methanol:ethyl acetate=1:4, V/V). After the reaction is stopped, the precipitate is filtered, the filter residue is washed with dichloromethane, the filtrates are combined, diluted with 100 mL of water, extracted with dichloromethane for three times, the organic layers are combined, concentrated under reduced pressure, then the concentrate is dissolved in 30 mL of anhydrous ethanol, heated to reflux, after the solution is clarified, 16 mL of concentrated hydrochloric acid is added under reflux, then yellow solid is precipitated, the reaction is continued for 2 hours, cooled, and filtered to obtain the crude product 3-hydroxy-3',4',5',5,7-pentamethoxy myricetin (intermediate a), yield: 54.4%.

(2) Preparation of 3-(3-bromopropoxy)-5,7-dimethoxy-2-(3,4,5-trimethoxyphenyl)-4H-chromene-4-one (intermediate b): 1.17 g (3 mmol)-3-hydroxy-3',4',5',5,7-pentamethoxy myricetin (intermediate a), 1.66 g K2CO3 (12 mmol) and 30 mL DMF are sequentially added into a 100 mL single-necked round bottom flask and stirred at room temperature for 0.5-1 h, then 2.42 g 1,3-dibromopropane (12 mmol) is added, and the reaction is stirred at room temperature for 12 h. TLC is used to monitor the reaction (ethyl acetate). After the reaction is completed, the reaction solution is dispersed with 50 mL of water, and white solid is separated out. Suction filtration is carried out. then the solid is added to a round bottom flask containing 30 mL of solution (ethyl acetate: n-hexane=3:1) and stirred at room temperature for 4-5 h, suction filtration is carried out, and vacuum column chromatography is carried out for separation and purification (petroleum ether: ethyl acetate=2:1, V/V) to obtain white solid (intermediate b), with a yield of 78.9%.

(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):

0.38 g (1.78 mmol) 4-(N-methyl)amino-N-Boc piperidine, 0.5 g (3.57 mol) K2CO3 and 40 mL acetonitrile are added into a 100 mL single-necked round-bottom flask, after the reaction mixture is stirred at room temperature for 0.5-1 h, 1 g(1.96 mmol) 3-(3-bromopropoxy)-5,7-dimethoxy-2-(3,4,5-trimethoxyphenyl)-4H-chromene-4-one (intermediate b) is added, then the reaction temperature is raised up to 80° C., and stirring at this temperature for 4-6 h. The reaction is monitored by TLC, when the reaction is finished, it is then cooled to room temperature, filtered to remove potassium carbonate and solid impurities, and the solvent is removed under reduced pressure to obtain a crude product (intermediate c) in the form of a burgundy oil for later use with yield:

(4) Preparation of hydrochloride (intermediate d) of 5,7-dimethoxy-3-(3-(methyl (piperidin-4-yl) amino) propoxy)-2-(3, 4, 5-trimethoxyphenyl)-4H-chromene-4-one:

In step (3), 4-((3-(5,7-dim ethoxy-4-oxo-2-(3,4,5-trimethoxyph enyl)-4H-chroman-3-yl)oxy)propyl)(methyl) aminotert-butyl)piperidine-1-carboxylic acid tert-butyl ester (intermediate c) is dissolved in about 30 mL methanol in a 100 mL single-necked round bottom flask, then 10 mL of 6 mol/L methanol hydrochloride solution is added, and stirred at room temperature for about 2 h. TLC followed the reaction. When the reaction is finished, the solvent is removed under reduced pressure, and a small amount of methanol is added to dissolve it. Then 20 mL of ethyl acetate is added. The mixture is continuously stirred until a yellow solid is separated out. The mixture is filtered, washed with ethyl acetate and dichloromethane respectively, and naturally dried to obtain a yellow solid (intermediate d), with a yield of 93.2%.

(5) Preparation of 4-chlorobenzyl-4-((3-((5,7-dimethoxy-4-oxo-2-(3,4,5-trimethoxyphenyl)-4H-chromene-3-yl)oxy) propyl)(methyl)amino)piperidine-1-dithiocarboxylic acid (target compound A1):

0.5 g (0.92 mmol) of hydrochloride (intermediate d) of 5,7-dimethoxy-3-(3-(methyl (piperidin-4-yl) amino) propoxy)-2-(3,4,5-trimethoxyphenyl)-4H-chromene-4-one, 0.25 g (1.84 mmol) of K2CO3 and 20 mL of acetonitrile are added to a 50 mL single-necked round bottom flask. After stirring for 1 h at room temperature, 0.7 g (9.21 mmol) of carbon disulfide is added dropwise under the ice bath. After stirring for 20 minutes, 0.15 g (0.92 mmol) of p-chlorobenzyl chloride is slowly added, then the reaction mixture is stirred for 2 h in ice bath. TLC followed the reaction and stopped the reaction when it is over. Poured the mixture into 100 mL of ice water, extracted with dichloromethane (3×20 mL), combined the organic layers, washed with saturated saline (3×20 mL), dried with anhydrous sodium sulfate, removed the solvent under reduced pressure to obtain the crude product, and purified by column chromatography (ethyl acetate: methanol=5:1~1:5, V/V) to obtain the target compound A1 with a yield of 74.7%.

Embodiment 2

The preparation method of 2-chlorobenzyl-4-((3-((5,7-dimethoxy-4-oxo-2-(3,4,5-trimethoxyphenyl)-4H-chromene-3-yl)oxy)propyl)(methyl)amino)piperidine-1-dithiocarboxylic acid (target compound A2) is as follows:

(1) Preparation of 3-hydroxy-3',4', 5', 5,7-pentamethoxy-myricetin (intermediate a):

As in step (1) of Embodiment 1.

(2) Preparation of 3-(3-bromopropoxy)-5,7-dim ethoxy-2-(3,4,5-trim ethoxyphenyl)-4H-chromene-4-one (intermediate b):

As in step (2) of Embodiment 1.

(3) Preparation of 4-((3-((5,7-dimethoxy-4-oxo-2-(3,4,5-trimethoxyphenyl)-4H-benzopyran-3-yl) oxy) propyl) (methyl)aminotert-butyl) piperidine-1-carboxylic acid tert-butyl ester (intermediate c):

As in step (3) of Embodiment 1.

(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:

As in step (4) of Embodiment 1.

(5) Preparation of 2-chlorobenzyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A2):

As in step (5) of Embodiment 1, the difference is that o-chlorobenzyl chloride is used as the raw material, and the yield is 75.1%.

Embodiment 3

The preparation method of 2,4-dichlorobenzyl 4-((3-((5, 7-dimethoxy-4-oxo-2-(3,4,5-trimethoxyphenyl)-4H-chromene-3-yl) oxy) propyl) (methyl) amino) piperidine-1-dithiocarboxylic acid (target compound A3) is as follows:

(1) Preparation of 3-hydroxy-3',4', 5',5,7-pentamethoxy myricetin (intermediate a):

As in step (1) of Embodiment 1.

(2) Preparation of 3-(3-bromopropoxy)-5,7-dim ethoxy-2-(3,4,5-trim ethoxyphenyl)-4H-chromene-4-one (intermediate b):

As in step (2) of Embodiment 1.

(3) Preparation of 4—((3-((5,7-dimethoxy-4-oxo-2-(3,4, 5-trimethoxyphenyl)-4H-benzopyran-3-yl) oxy) propyl) (methyl) amino tert-butyl) piperidine-1-carboxylic acid tert-butyl ester (intermediate c):

As in step (3) of Embodiment 1.

(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:

As in step (4) of Embodiment 1.

(5) Preparation of 2,4-dichlorobenzyl-4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A3):

As in step (5) of Embodiment 1, the difference is that 2,4-dichlorobenzyl chloride is used as the raw material, and the yield is 80.3%.

Embodiment 4

The preparation method of 2-fluorobenzyl 4-((3-((5,7-dimethoxy-4-oxo-2-(3,4,5-trimethoxyphenyl)-4H-chromene-3-yl)oxy)propyl)(methyl) amino) piperidine-1-dithiocarboxylic acid (target compound A4) is as follows:

(1) Preparation of 3-hydroxy-3', 4',5',5,7-Pentamethoxymyricetin (intermediate a):
As in step (1) of Embodiment 1;
(2) Preparation of 3-(3-bromopropoxy)-5,7-dim ethoxy-2-(3,4,5-trim ethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl)(methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
As in step (4) of Embodiment 1.
(5) Preparation of 2-fluorobenzyl 4-((3-((5,7-dim ethoxy-4-oxo-2-(3,4,5-trimethoxyphenyl)-4H-chromene-3-yl) oxy) propyl) (methyl) amino) piperidine-1-dithiocarboxylic acid (target compound A4):
As in step (5) of Embodiment 1, the difference is that o-fluorobenzyl chloride is used as the raw material, and the yield is 76.9%.

Embodiment 5

The preparation method of 3-methylbenzyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A5) is as follows:

(1) Preparation of 3-hydroxy-3', 4', 5', 5,7-pentamethoxy myricetin (intermediate a):
As in step (1) of Embodiment 1.
(2) Preparation of 3-(3-bromopropoxy)-5,7-dim ethoxy-2-(3,4,5-trim ethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3, 4,5-trimethoxyphenyl)-4H-chromene-4-one:
As in step (4) of Embodiment 1.
(5) Preparation of 3-methylbenzyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A5):
As in step (5) of Embodiment 1, the difference is that m-methyl benzyl chloride is used as the raw material, and the yield is 65.3%.

Embodiment 6

The preparation method of 2-methylbenzyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A6) is as follows:

(1) Preparation of 3-hydroxy-3', 4', 5', 5,7-pentamethoxy myricetin (intermediate a):
As in step (1) of Embodiment 1.
(2) Preparation of 3-(3-bromopropoxy)-5,7-dim ethoxy-2-(3,4,5-trim ethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c): As in step (3) of Embodiment 1.
(4) Preparation of hydrochloride (intermediate d) of 5,7-dimethoxy-3-(3-(methyl (piperidin-4-yl) amino) propoxy)-2-(3,4,5-trimethoxyphenyl)-4H-chromene-4-one:
As in step (4) of Embodiment 1.
(5) Preparation of 2-methylbenzyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A6):
As in step (5) of Embodiment 1, the difference is that o-methyl benzyl chloride is used as the raw material, and the yield is 44.4%.

Embodiment 7

The preparation method of 4-nitrobenzyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A7) is as follows:

(1) Preparation of 3-hydroxy-3', 4', 5', 5,7-pentamethoxy myricetin (intermediate a):
As in step (1) of Embodiment 1.
(2) Preparation of 3-(3-bromopropoxy)-5,7-dim ethoxy-2-(3,4,5-trim ethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3, 4,5-trimethoxyphenyl)-4H-chromene-4-one:
As in step (4) of Embodiment 1.
(5) Preparation of 4-nitrobenzyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A7):
As in step (5) of Embodiment 1, the difference is that p-nitrobenzyl chloride is used as the raw material, and the yield is 94.6%.

Embodiment 8

The preparation method of pyridine-3-ylmethyl 4-((3-((5, 7-dimethoxy-4-oxo-2-(3,4,5-trimethoxyphenyl)-4H-chromene-3-yl) oxy) propyl) (methyl) amino) piperidine-1-dithiocarboxylic acid (target compound A8) is as follows:

(1) Preparation of 3-hydroxy-3', 4', 5', 5,7-pentamethoxy myricetin (intermediate a):
As in step (1) of Embodiment 1.
(2) Preparation of 3-(3-bromopropoxy)-5,7-dim ethoxy-2-(3,4,5-trim ethoxyphenyl)-4H-chromene-4-one (intermediate b):
As in step (2) of Embodiment 1.

(3) Preparation of 44(3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3, 4,5-trimethoxyphenyl)-4H-chromene-4-one:
As in step (4) of Embodiment 1.
(5) Preparation of pyridine-3-ylmethyl 4-((3-((5,7-dimethoxy-4-oxo-2-(3,4,5-trimethoxyphenyl)-4H-chromene-3-yl) oxy) propyl) (methyl) amino) piperidine-1-dithiocarboxylic acid (target compound A8):
As in step (5) of Embodiment 1, the difference is that 3-(chloromethyl) pyridine is used as the raw material, and the yield is 65.2%.

Embodiment 9

The preparation method of (6-chloropyridine-3-yl) methyl 4-((3-((5,7-dimethoxy-4-oxo-2-(3,4,5-trimethoxyphenyl)-4H-benzopyran-3-yl) oxygen) propyl) (methyl) amino) piperidine-1-dithiocarboxylic acid (target compound A9) is as follows:
(1) Preparation of 3-hydroxy-3', 4', 5', 5, 7-pentamethoxy myricetin (intermediate a)
As in step (1) of Embodiment 1.
(2) Preparation of 3-(3-bromopropoxy)-5,7-dim ethoxy-2-(3,4,5-trim ethoxyphenyl)-4H-chromene-4-one (intermediate b):
As in step (2) of Embodiment 1.
(3) Preparation of 4-((3-((5,7-dimethoxy-4-oxo-2-(3,4,5-trimethoxyphenyl)-4H-benzopyran-3-yl) oxy) propyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(3-(methyl (piperidin-4-yl) amino) propoxy)-2-(3, 4,5-trimethoxyphenyl)-4H-chromene-4-one:
As in step (4) of Embodiment 1.
(5) Preparation of (6-chloropyridine-3-yl) methyl 4-((3-((5,7-dimethoxy-4-oxo-2-(3,4,5-trimethoxyphenyl)-4H-benzopyran-3-yl) oxygen) propyl) (methyl) amino) piperidine-1-dithiocarboxylic acid (target compound A9):
As in step (5) of Embodiment 1, the difference is that 2-chloro-5-(chloromethyl) pyridine is used as the raw material, and the yield is 53.0%.

Embodiment 10

The preparation method of 4-chlorobenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A10) is as follows:
(1) Preparation of 3-hydroxy-3', 4', 5', 5,7-pentamethoxy myricetin (intermediate a):
As in step (1) of Embodiment 1.
(2) Preparation of 3-(4-bromobutoxy)-5,7-dim ethoxy-2-(3,4,5-trim ethoxyphenyl)-4H-chromene-4-one (intermediate b):
As in step (2) of Embodiment 1. The difference is that 1,4-dibromobutane is used as a raw material.
(3) Preparation of 4-(4-((5,7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(4-(methyl (piperidin-4-yl) amino) butoxy)-2-(3, 4,5-trimethoxyphenyl)-4H-chromene-4-one:
As in step (4) of Embodiment 1.
(5) Preparation of 4-chlorobenzyl-4-((4-((5,7-dim ethoxy-4-oxo-2-(3,4,5-trimethoxyphenyl)-4H-benzopyran-3-yl) oxy) butyl) (methyl) amino) piperidine-1-dithiocarboxylic acid (target compound A10):
As in step (5) of Embodiment 1, the yield is 34.3%.

Embodiment 11

The preparation method of 2-chlorobenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A11) is as follows:
(1) Preparation of 3-hydroxy-3', 4', 5', 5,7-pentamethoxy myricetin (intermediate a):
As in step (1) of Embodiment 1.
(2) Preparation of 3-(4-bromobutoxy)-5,7-dim ethoxy-2-(3,4,5-trim ethoxyphenyl)-4H-chromene-4-one (intermediate b):
As in step (2) of Embodiment 10.
(3) Preparation of 4-(4-((5,7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(4-(methyl (piperidin-4-yl) amino) butoxy)-2-(3, 4,5-trimethoxyphenyl)-4H-chromene-4-one:
As in step (4) of Embodiment 1.
(5) Preparation of 2-chlorobenzyl-4-((4-((5,7-dim ethoxy-4-oxo-2-(3,4,5-trimethoxyphenyl)-4H-benzopyran-3-yl) oxy) butyl) (methyl) amino) piperidine-1-dithiocarboxylic acid (target compound A11):
As in step (5) of Embodiment 2, the yield is 28.6%.

Embodiment 12

The preparation method of 2,4-dichlorobenzyl-4-((4-((5, 7-dim ethoxy-4-oxo-2-(3,4,5-trimethoxyphenyl)-4H-benzopyran-3-yl) oxy) butyl) (methyl) amino) piperidine-1-dithiocarboxylic acid (target compound A12) is as follows:
(1) Preparation of 3-hydroxy-3', 4', 5', 5,7-pentamethoxy myricetin (intermediate a)
As in step (1) of Embodiment 1.
(2) Preparation of 3-(4-bromobutoxy)-5,7-dim ethoxy-2-(3,4,5-trim ethoxyphenyl)-4H-chromene-4-one (intermediate b):
As in step (2) of Embodiment 10.
(3) Preparation of 4-(4-((5,7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate c):
As in step (3) of Embodiment 1.
(4) Preparation of hydrochloride (intermediate d) of 5,7-dimethoxy-3-(4-(methyl (piperidin-4-yl) amino) butoxy)-2-(3, 4,5-trimethoxyphenyl)-4H-chromene-4-one:
As in step (4) of Embodiment 1.
(5) Preparation of 2,4-dichlorobenzyl-4-((4-((5,7-dim ethoxy-4-oxo-2-(3,4,5-trimethoxyphenyl)-4H-benzopyran-3-yl) oxy) butyl) (methyl) amino) piperidine-1-dithiocarboxylic acid (target compound A12):
As in step (5) of Embodiment 3, the yield is 31.3%.

Embodiment 13

The preparation method of 2-fluorobenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A13) is as follows:

(1) Preparation of 3-hydroxy-3', 4', 5', 5,7-pentamethoxy myricetin (intermediate a):

As in step (1) of Embodiment 1.

(2) Preparation of 3-(4-bromobutoxy)-5,7-dim ethoxy-2-(3,4,5-trim ethoxyphenyl)-4H-chromene-4-one (intermediate b):

As in step (2) of Embodiment 10.

(3) Preparation of 4-(4-((5,7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate c):

As in step (3) of Embodiment 1.

(4) Preparation of hydrochloride (intermediate d) of 5,7-dimethoxy-3-(4-(methyl (piperidin-4-yl) amino) butoxy)-2-(3, 4,5-trimethoxyphenyl)-4H-chromene-4-one:

As in step (4) of Embodiment 1.

(5) Preparation of 2-fluorobenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A13):

As in step (5) of Embodiment 4, the yield is 39.9%.

Embodiment 14

The preparation method of 3-methylbenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A14) is as follows:

(1) Preparation of 3-hydroxy-3', 4', 5', 5,7-pentamethoxy myricetin (intermediate a):

As in step (1) of Embodiment 1.

(2) Preparation of 3-(4-bromobutoxy)-5,7-dim ethoxy-2-(3,4,5-trim ethoxyphenyl)-4H-chromene-4-one (intermediate b):

As in step (2) of Embodiment 10.

(3) Preparation of 4-(4-((5,7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate C):

As in step (3) of Embodiment 1.

(4) Preparation of hydrochloride (intermediate d) of 5,7-dimethoxy-3-(4-(methyl (piperidin-4-yl) amino) butoxy)-2-(3, 4, 5-trimethoxyphenyl)-4H-chromene-4-one:

As in step (4) of Embodiment 1.

(5) Preparation of 3-methylbenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A14):

As in step (5) of Embodiment 5, the yield is 48.4%.

Embodiment 15

The preparation method of 2-methylbenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A15) is as follows:

(1) Preparation of 3-hydroxy-3', 4', 5', 5, 7-pentamethoxy myricetin (intermediate a):

As in step (1) of Embodiment 1.

(2) Preparation of 3-(4-bromobutoxy)-5,7-dim ethoxy-2-(3,4,5-trim ethoxyphenyl)-4H-chromene-4-one (intermediate b).

As in step (2) of Embodiment 10.

(3) Preparation of 4-(4-((5,7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate c):

As in step (3) of Embodiment 1.

(4) Preparation of hydrochloride (intermediate d) of 5,7-dimethoxy-3-(4-(methyl (piperidin-4-yl) amino) butoxy)-2-(3,4,5-trimethoxyphenyl)-4H-chromene-4-one:

As in step (4) of Embodiment 1.

(5) Preparation of 2-methylbenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A15):

As in step (5) of Embodiment 6, the yield is 57.7%.

Embodiment 16

The preparation method of 4-nitrobenzyl-4-((4-((5,7-dimethoxy-4-oxo-2-(3,4,5-trimethoxyphenyl)-4H-benzopyran-3-yl) oxy) butyl) (methyl) amino) piperidine-1-dithiocarboxylic acid (target compound A16) is as follows:

(1) Preparation of 3-hydroxy-3', 4', 5', 5, 7-pentamethoxy myricetin (intermediate a):

As in step (1) of Embodiment 1.

(2) Preparation of 3-(4-bromobutoxy)-5,7-dimethoxy-2-(3,4, 5-tri m ethoxyphenyl)-4H-chromene-4-one (intermediate b):

As in step (2) of Embodiment 10.

(3) Preparation of 4-(4-((5, 7-dimethoxy-4-oxo-2-(3,4,5-tri m ethoxyphenyl)-4H-benzopyran-3-yl) oxy) butyl) (methyl) amino tert-butyl) piperidine-1-carboxylic acid tert-butyl ester (intermediate c):

As in step (3) of Embodiment 1.

(4) Preparation of hydrochloride (intermediate d) of 5,7-dimethoxy-3-(4-(methyl (piperidin-4-yl) amino) butoxy)-2-(3, 4, 5-trimethoxyphenyl)-4H-chromene-4-one:

As in step (4) of Embodiment 1.

(5) Preparation of 4-nitrobenzyl-4-((4-((5, 7-dimethoxy-4-oxo-2-(3,4, 5-tri m ethoxyphenyl)-4H-benzopyran-3-yl) oxy) butyl) (methyl) amino) piperidine-1-dithiocarboxylic acid (target compound A16):

As in step (5) of Embodiment 7, the yield is 47.6%.

Embodiment 17

The preparation method of pyridine-3-ylmethyl-4-((4-((5, 7-dimethoxy-4-oxo-2-(3,4,5-trimethoxyphenyl)-4H-benzopyran-3-yl) oxy) butyl) (methyl) amino) piperidine-1-dithiocarboxylic acid (target compound A17) is as follows:

(1) Preparation of 3-hydroxy-3',4',5',5,7-pentamethoxy myricetin (intermediate a):

As in step (1) of Embodiment 1.

(2) Preparation of 3-(4-bromobutoxy)-5, 7-dim ethoxy-2-(3,4, 5-trim ethoxyphenyl)-4H-chromene-4-one (intermediate b):

As in step (2) of Embodiment 10.

(3) Preparation of 4-(4-((5, 7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate c):

As in step (3) of Embodiment 1.

(4) Preparation of hydrochloride (intermediate d) of 5,7-dimethoxy-3-(4-(methyl (piperidin-4-yl) amino) butoxy)-2-(3, 4, 5-trimethoxyphenyl)-4H-chromene-4-one:

As in step (4) of Embodiment 1.

(5) Preparation of pyridine-3-ylmethyl-4-((4-((5,7-dimethoxy-4-oxo-2-(3,4, 5-trimethoxyphenyl)-4H-benzopyran- 3-yl) oxy) butyl) (methyl) amino) piperidine-1-dithiocarboxylic acid (target compound A19):

As in step (5) of Embodiment 8, the yield is 50.5%.

Embodiment 18

The preparation method of (6-chloropyridine-3-yl) methyl-4-((4-((5,7-dimethoxy-4-oxo-2-(3, 4, 5-trimethoxyphenyl)-4H-benzopyran-3-yl) oxy) butyl) (methyl) amino) piperidine-1-dithiocarboxylic acid (target compound A18) is as follows:

(1) Preparation of 3-hydroxy-3', 4', 5', 5, 7-pentamethoxy myricetin (intermediate a):

As in step (1) of Embodiment 1.

(2) Preparation of 3-(4-bromobutoxy)-5, 7-dim ethoxy-2-(3,4, 5-trim ethoxyphenyl)-4H-chromene-4-one (intermediate b):

As in step (2) of Embodiment 10.

(3) Preparation of 4-(4-((5, 7-dim ethoxy-4-oxo-2-(3,4,5-trim ethoxyphenyl)-4H-benzopyran-3-yl) oxy) butyl) (methyl) amino tert-butyl) piperidine-1-carboxylic acid tert-butyl ester (intermediate c):

As in step (3) of Embodiment 1.

(4) Preparation of hydrochloride (intermediate d) of 5,7-dimethoxy-3-(4-(methyl (piperidin-4-yl) amino) butoxy)-2-(3,4, 5-trimethoxyphenyl)-4H-chromene-4-one: As in step (4) of Embodiment 1.

(5) Preparation of (6-chloropyridine-3-yl) methyl-4-((4-((5,7-dimethoxy-4-oxo-2-(3,4, 5-trimethoxyphenyl)-4H-benzopyran-3-yl) oxy) butyl) (methyl) amino) piperidine-1-dithiocarboxylic acid (target compound A20):

As in step (5) of Embodiment 9, the yield is 38.1%.

The physical and chemical properties and mass spectrum data of the synthesized dithiocarbamate-containing 4-(N-methyl) aminopiperidine myricetin derivative are shown in Table 1, and the nuclear magnetic resonance hydrogen spectrum (1H NMR) and carbon spectrum (13C NMR) data are shown in Table 2.

TABLE 1

Physical and Chemical Properties of Compound A Prepared in Embodiments 1-18

| Compound | n | R-group | Mass Spectrometry Data, m/z (calcd) | Character | Melting Point/° C. | Yield/% |
|---|---|---|---|---|---|---|
| $A_1$ | 3 | 4-Chlorobenzyl | 743.22211 (743.22221[M + N]$^+$) | Yellow Solid | 117.4-118.4 | 74.7 |
| $A_2$ | 3 | 2-Chlorobenzyl | 743.22028 (743.22221[M + N]$^+$) | White Solid | 133.5-133.9 | 75.3 |
| $A_3$ | 3 | 2,4-Dichlorobenzyl | 777.18158 (777.18324[M + N]$^+$) | White Solid | 146.5-147.2 | 80.3 |
| $A_4$ | 3 | 2-Fluorobenzyl | 727.25000 (727.25176[M + N]$^+$) | White Solid | 84.6-85.7 | 76.9 |
| $A_5$ | 3 | 3-Methylbenzyl | 723.27478 (723.27683[M + N]$^+$) | Yellow Solid | 106.8-107.2 | 65.3 |
| $A_6$ | 3 | 2-Methylbenzyl | 723.27543 (723.27683[M + N]$^+$) | Yellow Solid | 97.7-98.1 | 44.4 |
| $A_7$ | 3 | 4-Nirtobenzyl | 754.24445 (754.24626[M + N]$^+$) | Grey Solid | 141.2-142.9 | 94.6 |
| $A_8$ | 3 | Pyridine-3-Ylmethyl | 710.25648 (710.25643[M + N]$^+$) | Yellow Solid | 107.4-107.9 | 65.2 |
| $A_9$ | 3 | (4-Chloropyridine-3-yl)Methyl | 744.21564 (744.21746[M + N]$^+$) | Yellow Solid | 93.2-93.8 | 53.0 |
| $A_{10}$ | 4 | 4-Chlorobenzyl | 757.23700 (757.23786[M + N]$^+$) | White Solid | 116.9-117.2- | 34.3 |
| $A_{11}$ | 4 | 2-Chlorobenzyl | 757.23590 (757.23786[M + N]$^+$) | Yellow Solid | 96.9-97.4 | 28.6 |
| $A_{12}$ | 4 | 2,4-Dichlorobenzyl | 791.19714 (791.19889[M + N]$^+$) | Yellow Solid | 101.7-102.1 | 31.3 |
| $A_{13}$ | 4 | 2-Fluorobenzyl | 741.26563 (741.26741[M + N]$^+$) | Yellow Oily | — | 39.9 |
| $A_{14}$ | 4 | 3-Methylbenzyl | 737.29053 (737.29248[M + N]$^+$) | Yellow Oily | — | 48.4 |
| $A_{15}$ | 4 | 2-Methylbenzyl | 737.29010 (737.29248[M + N]$^+$) | Yellow Oily | — | 57.7 |
| $A_{16}$ | 4 | 4-Nirtobenzyl | 768.26050 (768.26191[M + N]$^+$) | Red Oil | — | 47.6 |
| $A_{17}$ | 4 | Pyridine-3-Ylmethyl | 724.27008 (724.27208[M + N]$^+$) | Red Oil | — | 50.5 |
| $A_{18}$ | 4 | (6-Chloropyridine-3-yl)Methyl | 758.23053 (758.23311[M + N]$^+$) | Red Oil | — | 38.1 |

TABLE 2 nuclear magnetic resonance spectrum data of compound A prepared in Embodiments 1-18

| Compound | $^1$H NMR, $^{13}$C NMR (TMS as internal standard) |
|---|---|
| $A_1$ | $^1$H NMR (400 MHz, DMSO) δ 7.41 (d, J = 8.5 Hz, 2H, Ph—H), 7.36 (t, J = 4.2 Hz, 4H, Ph—H), 6.83 (d, J = 2.1 Hz, 1H, Ph—H), 6.49 (d, J = 2.0 Hz, 1H, Ph—H), 5.32-5.21 (m, 1H, Piperidinyl-H), 4.52 (d, J = 5.7 Hz, 2H, —S—CH$_2$—), 4.47-4.36 (m, 1H, Piperidinyl-H), 3.98 (t, J = 6.1 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.20 (dt, J = 40.6, 11.1 Hz, 2H, Piperidinyl-H), 2.65-2.55 (m, 1H, Piperidinyl-H), 2.42 (s, 2H, —O—CH$_2$CH$_2$CH$_2$—N—), 2.07 (s, 3H, N—CH$_3$), 1.72 (dd, J = 18.5, 11.1 Hz, 4H, —O—CH$_2$CH$_2$CH$_2$—N—, Piperidinyl-H), 1.36-1.22 (m, 2H, Piperidinyl-H).<br>$^{13}$C NMR (101 MHz, DMSO) δ 193.83, 172.68, 164.20, 160.76, 158.63, 153.15, 152.01, 140.47, 139.85, 136.26, 132.35, 131.45, 128.83, 126.14, 108.95, 106.33, 96.38, 93.56, 70.74, 60.68, 59.88, 56.57, 56.51, 51.20, 50.64, 49.39, 37.34, 28.54, 27.67. |
| $A_2$ | $^1$H NMR (400 MHz, DMSO) δ 7.61-7.56 (m, 1H, Ph—H), 7.49-7.45 (m, 1H, Ph—H), 7.36 (s, 2H, Ph—H), 7.34-7.29 (m, 2H, Ph—H), 6.83 (d, J = 2.0 Hz, 1H, Ph—H), 6.49 (d, J = 2.1 Hz, 1H, Ph—H), 5.32-5.20 (m, 1H, Piperidinyl-H), 4.59 (d, J = 7.6 Hz, 2H, —S—CH$_2$—), 4.45-4.35 (m, 1H, Piperidinyl-H), 3.98 (t, J = 6.1 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.20 (dt, J = 41.7, 11.1 Hz, 2H, Piperidinyl-H), 2.63-2.54 (m, 1H, Piperidinyl-H), 2.41 (t, J = 7.0 Hz, 2H, CH$_2$, —O—CH$_2$CH$_2$CH$_2$—N—), 2.06 (s, 3H, N—CH$_3$), 1.77-1.65 (m, 4H, —O—CH$_2$CH$_2$CH$_2$—N—, Piperidinyl-H), 1.39-1.26 (m, 2H, Piperidinyl-H). |

TABLE 2-continued nuclear magnetic resonance spectrum data of compound A prepared in Embodiments 1-18

| Compound | $^1$H NMR, $^{13}$C NMR (TMS as internal standard) |
|---|---|
| | $^{13}$C NMR (101 MHz, DMSO) δ 193.56, 172.67, 164.19, 160.75, 158.63, 153.15, 151.99, 140.48, 139.83, 134.20, 133.93, 132.07, 129.97, 129.90, 127.84, 126.15, 108.95, 106.32, 96.38, 93.55, 70.74, 60.68, 59.84, 56.56, 51.10, 50.58, 49.44, 37.34, 28.55, 28.04, 27.68. |
| A$_3$ | $^1$H NMR (400 MHz, DMSO) δ 7.64 (d, J = 2.0 Hz, 1H, Ph—H), 7.61 (d, J = 8.3 Hz, 1H, Ph—H), 7.40 (dd, J = 8.3, 2.0 Hz, 1H, Ph—H), 7.37 (s, 2H, Ph—H), 6.83 (d, J = 1.8 Hz, 1H, Ph—H), 6.49 (d, J = 1.9 Hz, 1H, Ph—H), 5.24 (d, J = 10.4 Hz, 1H, Piperidinyl-H), 4.58 (d, J = 7.6 Hz, 2H, —S—CH$_2$—), 4.41 (d, J = 11.6 Hz, 1H, Piperidinyl-H), 3.98 (t, J = 6.0 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.20 (dt, J = 22.1, 11.6 Hz, 2H, Piperidinyl-H), 2.57 (d, J = 9.9 Hz, 1H, Piperidinyl-H), 2.41 (t, J = 6.4 Hz, 2H, —O—CH$_2$CH$_2$CH$_2$—N—), 2.06 (s, 3H, N—CH$_3$), 1.72 (dd, J = 18.5, 11.1 Hz, 4H, —O—CH$_2$CH$_2$CH$_2$—N—, Piperidinyl-H), 1.32 (s, 2H, Piperidinyl-H). $^{13}$C NMR (101 MHz, DMSO) δ 193.20, 172.67, 164.19, 160.73, 158.63, 153.14, 151.99, 140.47, 139.79, 134.87, 133.67, 133.51, 133.16, 129.35, 127.96, 126.14, 108.92, 106.27, 96.37, 93.54, 70.73, 60.68, 59.83, 56.55, 56.51, 50.57, 38.72, 37.34, 36.25, 31.23, 28.54. |
| A$_4$ | $^1$H NMR (400 MHz, DMSO) δ 7.51 (td, J = 7.7, 1.6 Hz, 1H, Ph—H), 7.38-7.31 (m, 3H, Ph—H), 7.23-7.14 (m, 2H, Ph—H), 6.83 (d, J = 2.1 Hz, 1H, Ph—H), 6.49 (d, J = 2.2 Hz, 1H, Ph—H), 5.26 (d, J = 10.8 Hz, 1H, Piperidinyl-H), 4.51 (d, J = 5.6 Hz, 2H, —S—CH$_2$—), 4.41 (d, J = 12.5 Hz, 1H, Piperidinyl-H), 3.98 (t, J = 6.1 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.28-3.09 (m, 2H, Piperidinyl-H), 2.57 (d, J = 11.0 Hz, 1H, Piperidinyl-H), 2.41 (t, J = 6.8 Hz, 2H, —O—CH$_2$CH$_2$CH$_2$—N—), 2.06 (s, 3H, N CH$_3$), 1.76-1.65 (m, 4H, —O—CH$_2$CH$_2$CH$_2$—N—, Piperidinyl-H), 1.38-1.25 (m, 2H, Piperidinyl-H). $^{13}$C NMR (101 MHz, DMSO) δ 193.51, 172.68, 164.19, 160.74, 159.70, 158.63, 153.14, 152.00, 140.47, 139.80, 132.02, 131.98, 130.27, 130.18, 126.14, 124.99, 124.96, 123.61, 123.46, 115.94, 115.73, 108.93, 106.28, 96.38, 93.54, 70.73, 60.67, 59.85, 56.55, 56.50, 50.58 49.40, 37.32, 34.93, 28.54, 27.63. $^{19}$F NMR (376 MHz, DMSO) δ −116.89; |
| A$_5$ | $^1$H NMR (400 MHz, DMSO) δ 7.36 (s, 2H, Ph—H), 7.23-7.15 (m, 3H, Ph—H), 7.07 (d, J = 6.8 Hz, 1H, Ph—H), 6.83 (d, J = 1.9 Hz, 1H, Ph—H), 6.49 (d, J = 2.1 Hz, 1H, Ph—H), 5.28 (d, J = 9.9 Hz, 1H, Piperidinyl-H), 4.44 (t, J = 9.1 Hz, 3H, —S—CH$_2$—, Piperidinyl-H), 3.98 (t, J = 6.1 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.18 (dt, J = 40.8, 11.0 Hz, 2H, Piperidinyl-H), 2.59 (t, J = 11.0 Hz, 1H, Piperidinyl-H), 2.41 (t, J = 6.7 Hz, 2H, —O—CH$_2$CH$_2$CH$_2$—N—), 2.27 (s, 3H, Ph—CH$_3$), 2.06 (s, 3H, N—CH$_3$), 1.78-1.63 (m, 4H, —O—CH$_2$CH$_2$CH$_2$—N—, Piperidinyl-H), 1.33 (s, 2H, Piperidinyl-H). $^{13}$C NMR (101 MHz, DMSO) δ 194.18, 172.68, 164.19, 160.75, 158.63, 153.14, 152.00, 140.48, 139.82, 138.10, 136.47, 130.24, 128.85, 128.48, 126.78, 126.14, 108.94, 106.30, 96.37, 93.55, 70.74, 60.68, 59.90, 56.56, 56.50, 50.58, 49.36, 41.63, 37.33, 28.56, 27.69, 21.38. |
| A$_6$ | $^1$H NMR (400 MHz, DMSO) δ 7.36 (s, 2H, Ph—H), 7.26 (d, J = 8.0 Hz, 2H, Ph—H), 7.11 (d, J = 7.9 Hz, 2H, Ph—H), 6.83 (d, J = 2.1 Hz, 1H, Ph—H), 6.49 (d, J = 2.2 Hz, 1H, Ph—H), 5.28 (d, J = 9.9 Hz, 1H, Piperidinyl-H), 4.43 (dd, J = 14.4, 3.7 Hz, 3H, —S—CH$_2$—, Piperidinyl-H), 3.98 (t, J = 6.1 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.26-3.08 (m, 2H, Piperidinyl-H), 2.58 (t, J = 11.0 Hz, 1H, Piperidinyl-H), 2.41 (t, J = 7.0 Hz, 2H, —O—CH$_2$CH$_2$CH$_2$—N—), 2.27 (s, 3H, Ph—CH$_3$), 2.06 (s, 3H, N—CH$_3$), 1.78-1.63 (m, 4H, —O—CH$_2$CH$_2$CH$_2$—N—, Piperidinyl-H), 1.33 (dd, J = 34.5, 15.1 Hz, 2H, Piperidinyl-H). $^{13}$C NMR (101 MHz, DMSO) δ 194.22, 172.67, 164.19, 160.74, 158.63, 153.14, 151.99, 140.48, 139.80, 137.05, 133.48, 129.60, 126.15, 108.93, 106.28, 96.38, 93.54, 70.74, 60.68, 59.90, 56.55, 56.51, 50.57, 49.30, 41.40, 37.33, 28.56, 27.66, 21.16. |
| A$_7$ | $^1$H NMR (400 MHz, DMSO) δ 8.17 (d, J = 8.8 Hz, 2H, Ph—H), 7.66 (d, J = 8.7 Hz, 2H, Ph—H), 7.37 (s, 2H, Ph—H), 6.83 (d, J = 2.2 Hz, 1H, Ph—H), 6.49 (d, J = 2.2 Hz, 1H, Ph—H), 5.24 (d, J = 11.3 Hz, 1H, Piperidinyl-H), 4.71 (d, J = 8.2 Hz, 2H, —S—CH$_2$—), 4.45 (d, J = 12.0 Hz, 1H, Piperidinyl-H), 3.98 (t, J = 6.2 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.16 (d, J = 14.0 Hz, 2H, Piperidinyl-H), 2.60 (t, J = 11.0 Hz, 1H, Piperidinyl-H), 2.42 (t, J = 7.0 Hz, 2H, —O—CH$_2$CH$_2$CH$_2$—N—), 2.07 (s, 3H, N CH$_3$), 1.73 (dt, J = 18.6, 9.1 Hz, 4H, —O—CH$_2$CH$_2$CH$_2$—N—, Piperidinyl-H), 1.33 (d, J = 10.9 Hz, 2H, Piperidinyl-H). $^{13}$C NMR (101 MHz, DMSO) δ 193.29, 172.68, 164.20, 160.74, 158.63, 153.14, 152.01, 147.01, 145.85, 140.47, 139.81, 130.75, 126.14, 123.94, 108.93, 106.28, 96.38, 93.54, 70.73, 60.68, 59.82, 56.55, 56.51, 50.57, 49.07, 37.35, 36.25, 28.52, 27.66. |
| A$_8$ | $^1$H NMR (400 MHz, DMSO) δ 8.60 (d, J = 2.0 Hz, 1H, Pyridyl-H), 8.45 (dd, J = 4.8, 1.5 Hz, 1H, Pyridyl-H)), 7.79 (dt, J = 7.8, 1.8 Hz, 1H, Pyridyl-H), 7.36 (s, 2H, Ph—H), 7.34 (dd, J = 7.9, 4.8 Hz, 1H, Pyridyl-H), 6.83 (d, J = 2.2 Hz, 1H, Ph—H), 6.49 (d, J = 2.2 Hz, 1H, Ph—H), 5.25 (d, J = 10.1 Hz, 1H, Piperidinyl-H), 4.56 (d, J = 5.0 Hz, 2H, —S—CH$_2$—), 4.43 (d, J = 11.6 Hz, 1H, Piperidinyl-H), 3.98 (t, J = 6.1 Hz, 2H, —O—CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.20 (dt, J = 22.8, 11.9 Hz, 2H, Piperidinyl-H), 2.59 (t, J = 10.9 Hz, 1H, Piperidinyl-H), 2.42 (t, J = 6.8 Hz, 2H, —O—CH$_2$CH$_2$CH$_2$—N—), 2.06 (s, 3H, N CH$_3$), 1.78-1.65 (m, 4H, —O—CH$_2$CH$_2$CH$_2$—N—, Piperidinyl-H), 1.34 (s, 2H, Piperidinyl-H). $^{13}$C NMR (101 MHz, DMSO) δ 193.57, 172.68, 164.20, 160.75, 158.63, 153.15, 152.00, 150.54, 148.83, 140.47, 139.84, 137.14, 133.25, 128.14, 123.93, 108.94, 106.32, 96.38, 93.56, 70.74, 60.68, 59.84, 56.57, 56.51, 50.59, 49.46, 38.22, 37.34, 28.54, 28.09. |

TABLE 2-continued nuclear magnetic resonance spectrum data of compound A prepared in Embodiments 1-18

| Compound | $^1$H NMR, $^{13}$C NMR (TMS as internal standard) |
|---|---|
| $A_9$ | $^1$H NMR (400 MHz, DMSO) δ 8.43 (d, J = 2.3 Hz, 1H, Pyridyl-H), 7.86 (dd, J = 8.3, 2.5 Hz, 1H, Pyridyl-H)), 7.47 (d, J = 8.2, 1H, Pyridyl-H), 7.36 (s, 2H, Ph—H), 6.83 (d, J = 2.2 Hz, 1H, Ph—H), 6.49 (d, J = 2.2 Hz, 1H, Ph—H), 5.23 (d, J = 10.2 Hz, 1H, Piperidinyl-H), 4.57 (d, J = 4.4 Hz, 2H, —S—CH$_2$—), 4.42 (d, J = 12.5 Hz, 1H, Piperidinyl-H), 3.98 (t, J = 6.1 Hz, 2H, —O—CH$_2$CH$_2$CH$_2$—N—), 3.90 (s, 3H, Ph—OCH$_3$), 3.87 (s, 6H, Ph—OCH$_3$), 3.85 (s, 3H, Ph—OCH$_3$), 3.75 (s, 3H, Ph—OCH$_3$), 3.21 (dt, J = 21.4, 11.8 Hz, 2H, Piperidinyl-H), 2.59 (t, J = 10.5 Hz, 1H, Piperidinyl-H), 2.42 (t, J = 6.6 Hz, 2H, —O—CH$_2$CH$_2$CH$_2$—N—), 2.06 (s, 3H, N—CH$_3$), 1.77-1.64 (m, 4H, —O—CH$_2$CH$_2$CH$_2$—N—, Piperidinyl-H), 1.32 (d, J = 10.3 Hz, 2H, Piperidinyl-H);<br>$^{13}$C NMR (101 MHz, DMSO) δ 193.26, 172.68, 164.20, 160.75, 158.63, 153.15, 152.01, 150.64, 149.41, 140.79, 139.84, 133.28, 126.14, 124.46, 108.94, 106.32, 96.38, 93.56, 70.74, 60.68, 59.81, 56.57, 56.51, 55.39, 50.58, 37.34, 37.12, 28.53, 27.87. |
| $A_{10}$ | $^1$H NMR (400 MHz, DMSO) δ 7.44-7.34 (m, 6H, Ph—H), 6.83 (d, J = 2.2 Hz, 1H, Ph—H), 6.49 (d, J = 2.2 Hz, 1H, Ph—H), 5.27 (d, J = 11.2 Hz, 1H, Piperidinyl-H), 4.53 (d, J = 7.5 Hz, 2H, —S—CH$_2$—), 4.43 (d, J = 12.6 Hz, 1H, Piperidinyl-H), 3.94 (t, J = 6.5 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.33-3.23 (m, 1H, Piperidinyl-H), 3.22-3.14 (m, 1H, Piperidinyl-H), 2.65 (ddd, J = 13.9, 7.1, 3.2 Hz, 1H, Piperidinyl-H), 2.32 (t, J = 6.9 Hz, 2H, —O—CH$_2$CH$_2$CH$_2$CH$_2$—N—), 2.07 (s, 3H, N—CH$_3$), 1.73 (d, J = 11.4 Hz, 2H, —O—CH$_2$CH$_2$CH$_2$CH$_2$—N—), 1.68-1.58 (m, 2H, Piperidinyl-H), 1.44 (dd, J = 14.3, 7.2 Hz, 2H, Piperidinyl-H), 1.40-1.25 (m, 2H, —O—CH$_2$CH$_2$CH$_2$CH$_2$—N—);<br>$^{13}$C NMR (101 MHz, DMSO) δ 193.74, 172.69, 164.19, 160.73, 158.62, 153.12, 151.96, 140.45, 139.79, 136.28, 132.35, 131.46, 128.83, 126.13, 108.92, 106.17, 96.36, 93.54, 72.09, 60.65, 59.73, 56.54, 56.51, 52.99, 51.24, 49.45, 37.56, 28.15, 27.87, 24.00. |
| $A_{11}$ | $^1$H NMR (400 MHz, DMSO) δ 7.59 (dd, J = 6.7, 2.4 Hz, 1H, Ph—H), 7.51-7.46 (m, 1H, Ph—H), 7.39 (s, 2H, Ph—H), 7.36-7.29 (m, 2H, Ph—H), 6.85 (d, J = 1.7 Hz, 1H, Ph—H), 6.49 (d, J = 1.8 Hz, 1H, Ph—H), 5.36 (s, 1H, Piperidinyl-H), 4.60 (d, J = 6.5, 2H, —S—CH$_2$—), 4.50 (s, 1H, Piperidinyl-H), 3.94 (t, J = 5.6 Hz, 2H, —O—CH$_2$CH$_2$CH$_2$CH$_2$—N—), 3.90 (s, 3H, Ph—OCH$_3$), 3.88 (s, 6H, Ph—OCH$_3$), 3.84 (s, 3H, Ph—OCH$_3$), 3.76 (s, 3H, Ph—OCH$_3$), 3.21 (d, J = 11.0 Hz, 2H, Piperidinyl-H), 2.68 (s, 1H, Piperidinyl-H), 2.34 (d, J = 9.6 Hz, 3H, CH$_2$, —O—CH$_2$CH$_2$CH$_2$CH$_2$—N—, Piperidinyl-H), 1.91 (s, 3H, N—CH$_3$), 1.54 (dd, J = 42.6, 36.0 Hz, 6H, —O—CH$_2$CH$_2$CH$_2$CH$_2$—N—, Piperidinyl-H), 1.34-1.15 (m, 1H, Piperidinyl-H).<br>$^{13}$C NMR (101 MHz, DMSO) δ 193.97, 172.71, 164.24, 160.74, 158.63, 153.16, 152.05, 140.35, 139.84, 134.09, 133.94, 132.10, 130.03, 129.92, 127.88, 126.08, 108.90, 106.15, 96.41, 93.58, 71.70, 60.67, 60.01, 56.57, 56.53, 52.74, 52.74, 52.74, 37.10, 27.58, 27.57, 27.54, 21.57. |
| $A_{12}$ | $^1$H NMR (400 MHz, DMSO) δ 7.63 (dd, J = 12.3, 5.2 Hz, 2H, Ph—H), 7.43-7.37 (m, 3H, Ph—H), 6.84 (d, J = 2.1 Hz, 1H, Ph—H), 6.49 (d, J = 2.2 Hz, 1H, Ph—H), 5.25 (d, J = 11.5 Hz, 1H, Piperidinyl-H), 4.59 (d, J = 7.5 Hz, 2H, —S—CH$_2$—), 4.42 (d, J = 12.5 Hz, 1H, Piperidinyl-H), 3.94 (t, J = 6.5 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.19 (t, J = 11.6 Hz, 1H, Piperidinyl-H), 2.65 (t, J = 10.8 Hz, 1H, Piperidinyl-H), 2.32 (t, J = 6.9 Hz, 2H, —O—CH$_2$CH$_2$CH$_2$CH$_2$—N—), 2.07 (s, 3H, N—CH$_3$), 1.74 (d, J = 11.5 Hz, 2H, —O—CH$_2$CH$_2$CH$_2$CH$_2$—N—), 1.62 (dd, J = 14.9, 7.3 Hz, 2H, —O—CH$_2$CH$_2$CH$_2$CH$_2$—N—), 1.43 (dt, J = 14.4, 7.3 Hz, 2H, Piperidinyl-H), 1.33 (t, J = 11.2 Hz, 2H, Piperidinyl-H), 1.24 (t, J = 6.5 Hz, 1H, Piperidinyl-H);<br>$^{13}$C NMR (101 MHz, DMSO) δ 193.17, 172.70, 164.20, 160.73, 158.63, 153.13, 151.99, 140.45, 139.80, 134.97, 133.70, 133.51, 133.16, 129.35, 127.96, 126.13, 108.92, 106.19, 96.38, 93.56, 72.10, 60.66, 59.68, 56.55, 56.52, 52.98, 49.56, 38.71, 37.58, 27.86, 27.71, 24.00. |
| $A_{13}$ | $^1$H NMR (400 MHz, DMSO) δ 7.51 (td, J = 7.7, 1.6 Hz, 1H, Ph—H), 7.38 (s, 2H, Ph—H), 7.37-7.31 (m, 1H, Ph—H), 7.17 (ddd, J = 8.9, 8.4, 5.0 Hz, 2H, Ph—H), 6.83 (d, J = 2.2 Hz, 1H, Ph—H), 6.49 (d, J = 2.2 Hz, 1H, Ph—H), 5.27 (d, J = 9.7 Hz, 1H, Piperidinyl-H), 4.52 (d, J = 4.3 Hz, 2H, —S—CH$_2$—), 4.42 (d, J = 11.1 Hz, 1H, Piperidinyl-H), 3.94 (t, J = 6.5 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.27-3.10 (m, 2H, Piperidinyl-H), 2.67 (t, J = 8.8 Hz, 1H, Piperidinyl-H), 2.34 (t, J = 6.7 Hz, 2H, —O—CH$_2$CH$_2$CH$_2$CH$_2$—N—), 2.08 (s, 3H, N—CH$_3$), 1.74 (d, J = 11.5 Hz, 2H, —O—CH$_2$CH$_2$CH$_2$CH$_2$—N—), 1.68-1.59 (m, 2H, —O—CH$_2$CH$_2$CH$_2$CH$_2$—N—), 1.49-1.40 (m, 2H, Piperidinyl-H), 1.33-1.21 (m, 2H, Piperidinyl-H).<br>$^{13}$C NMR (101 MHz, DMSO) δ 193.52, 172.69, 164.20, 162.15, 160.75, 159.71, 158.63, 153.14, 151.98, 140.45, 139.86, 132.00, 131.96, 130.25, 126.13, 124.98, 124.95, 123.65, 123.50, 115.93, 115.72, 108.95, 106.24, 96.37, 93.57, 72.09, 60.65, 59.73, 56.54, 56.50, 53.00, 49.44, 37.55, 34.92, 27.86, 23.98, 19.03.<br>$^{19}$F NMR (376 MHz, DMSO) δ −116.85; |
| $A_{14}$ | $^1$H NMR (400 MHz, DMSO) δ 7.38 (s, 2H, Ph—H), 7.22-7.15 (m, 3H, Ph—H), 7.09-7.05 (m, 1H, Ph—H), 6.83 (d, J = 2.2, 1H, Ph—H), 6.48 (d, J = 2.2 Hz, 1H, Ph—H), 5.29 (d, J = 9.6 Hz, 1H, Piperidinyl-H), 4.50-4.34 (m, 3H, —S—CH$_2$—, Piperidinyl-H), 3.94 (t, J = 6.4 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.20 (d, J = 19.5 Hz, 2H, Piperidinyl-H), 2.67 (s, 1H, Piperidinyl-H), 2.40-2.29 (m, 2H, —O—CH$_2$CH$_2$CH$_2$CH$_2$—N—), 2.27 (s, 3H, Ph—OCH$_3$), 2.09 (s, 3H, N—CH$_3$), 1.75 (d, J = 11.2 Hz, 2H, —O—CH$_2$CH$_2$CH$_2$CH$_2$—N—), 1.68-1.59 (m, 2H, —O—CH$_2$CH$_2$CH$_2$CH$_2$—N—), 1.41 (d, J = 30.1 Hz, 4H, Piperidinyl-H),. |

TABLE 2-continued nuclear magnetic resonance spectrum data of compound A prepared in Embodiments 1-18

| Compound | $^1$H NMR, $^{13}$C NMR (TMS as internal standard) |
|---|---|
| | $^{13}$C NMR (101 MHz, DMSO) δ 194.20, 172.69, 164.20, 160.75, 158.62, 153.14, 151.98, 140.45, 139.86, 138.10, 136.51, 130.23, 128.84, 128.47, 126.77, 126.13, 108.95, 106.24, 96.37, 93.56, 72.07, 60.66, 59.80, 56.54, 56.50, 53.00, 49.07, 41.62, 37.54, 27.85, 23.99, 21.38, 19.03. |
| $A_{15}$ | $^1$H NMR (400 MHz, DMSO) δ 7.38 (s, 2H, Ph—H), 7.26 (d, J = 8.0 Hz, 2H, Ph—H), 7.12 (d, J = 7.8 Hz, 2H, Ph—H), 6.83 (d, J = 2.2, 1H, Ph—H), 6.49 (d, J = 2.2 Hz, 1H, Ph—H), 5.29 (d, J = 9.7 Hz, 1H, Piperidinyl-H), 4.45 (d, J = 3.9 Hz, 3H, —S—CH$_2$—, Piperidinyl-H), 3.94 (t, J = 6.4 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.17 (s, 2H, Piperidinyl-H), 2.70 (s, 1H, Piperidinyl-H), 2.42-2.31 (m, 2H, —O—CH$_2$CH$_2$CH$_2$CH$_2$—N—), 2.27 (s, 3H, Ph—OCH$_3$), 2.11 (s, 3H, N—CH$_3$), 1.75 (d, J = 11.6 Hz, 2H, —O—CH$_2$CH$_2$CH$_2$CH$_2$—N—), 1.68-1.59 (m, 2H, —O—CH$_2$CH$_2$CH$_2$CH$_2$—N—), 1.42 (dd, J = 37.0, 6.8 Hz, 4H, Piperidinyl-H). $^{13}$C NMR (101 MHz, DMSO) δ 194.28, 172.69, 164.21, 160.76, 158.63, 153.15, 151.99, 140.44, 139.86, 137.04, 133.51, 129.63, 129.58, 129.54, 129.49, 126.13, 108.94, 106.24, 96.38, 93.57, 72.05, 60.66, 59.81, 56.55, 56.51, 52.99, 49.07, 41.40, 37.51, 27.84, 23.87, 21.16, 19.03. |
| $A_{16}$ | $^1$H NMR (400 MHz, DMSO) δ 8.21-8.14 (m, 2H, Ph—H), 7.66 (d, J = 8.8 Hz, 2H, Ph—H), 7.38 (s, 2H, Ph—H), 6.83 (d, J = 2.2 Hz, 1H, Ph—H), 6.49 (d, J = 2.2 Hz, 1H, Ph—H), 5.25 (d, J = 8.7 Hz, 1H, Piperidinyl-H), 4.71 (d, J = 7.9 Hz, 2H, —S—CH$_2$—), 4.46 (d, J = 10.7 Hz, 1H, Piperidinyl-H), 3.94 (t, J = 6.4 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.25-3.15 (m, 2H, Piperidinyl-H), 2.69 (s, 1H, Piperidinyl-H), 2.36 (s, 2H, —O—CH$_2$CH$_2$CH$_2$CH$_2$—N—), 2.10 (s, 3H, N—CH$_3$), 1.77 (d, J = 11.0 Hz, 2H, —O—CH$_2$CH$_2$CH$_2$CH$_2$—N—), 1.63 (dd, J = 14.2, 6.7 Hz, 2H, —O—CH$_2$CH$_2$CH$_2$CH$_2$—N—), 1.50-1.34 (m, 4H, Piperidinyl-H). $^{13}$C NMR (101 MHz, DMSO) δ 193.32, 172.69, 164.20, 160.75, 158.62, 153.14, 151.98, 147.02, 145.86, 140.45, 139.86, 137.04, 130.74, 126.13, 123.92, 108.94, 106.23, 96.37, 93.56, 72.06, 60.66, 59.71, 56.55, 56.50, 53.00, 49.07, 37.54, 36.24, 28.12, 27.85, 23.92. |
| $A_{17}$ | $^1$H NMR (400 MHz, DMSO) δ 8.60 (d, J = 1.8 Hz, 1H, Pyridyl-H), 8.46 (dd, J = 4.7, 1.5 Hz, 1H, Pyridyl-H), 7.80 (d, J = 7.8 Hz, 1H, Pyridyl-H), 7.38 (s, 2H, Ph—H), 7.34 (dd, J = 7.8, 4.6 Hz, 1H, Pyridyl-H), 6.84 (d, J = 2.1 Hz, 1H, Ph—H), 6.49 (d, J = 2.1 Hz, 1H, Ph—H), 5.26 (d, J = 11.4 Hz, 1H, Piperidinyl-H), 4.58-4.55 (m, 2H, —S—CH$_2$—), 4.44 (d, J = 13.1 Hz, 1H, Piperidinyl-H), 3.94 (t, J = 6.5 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.18 (dd, J = 15.1, 9.6 Hz, 2H, Piperidinyl-H), 2.65 (ddd, J = 11.0, 7.5, 3.7 Hz, 1H, Piperidinyl-H), 2.32 (t, J = 6.9 Hz, 2H, —O—CH$_2$CH$_2$CH$_2$CH$_2$—N—), 2.07 (s, 3H, N—CH$_3$), 1.87 (s, 1H, Piperidinyl-H), 1.74 (d, H = 11.7 Hz, 2H, —O—CH$_2$CH$_2$CH$_2$CH$_2$—N—), 1.44 (dd, J = 14.1, 7.1 Hz, 2H, —O—CH$_2$CH$_2$CH$_2$CH$_2$—N—), 1.33 (d, J = 20.7 Hz, 2H, Piperidinyl-H), 1.28-1.17 (m, 1H, Piperidinyl-H). $^{13}$C NMR (101 MHz, DMSO) δ 193.51, 172.69, 164.19, 160.73, 158.62, 153.13, 151.98, 150.54, 148.83, 140.45, 139.80, 137.15, 133.28, 126.13, 123.94, 108.92, 106.18, 96.37, 93.55, 72.10, 60.65, 59.70, 56.55, 55.40, 53.00, 38.20, 37.57, 27.87, 27.70, 24.00. |
| $A_{18}$ | $^1$H NMR (400 MHz, DMSO) δ 8.44 (d, J = 2.3 Hz, 1H, Pyridyl-H), 7.87 (dd, J = 8.3, 2.5 Hz, 1H, Pyridyl-H), 7.47 (d, J = 8.2 Hz, 1H, Pyridyl-H), 7.39 (s, 2H, Ph—H), 6.84 (d, J = 2.2 Hz, 1H, Ph—H), 6.49 (d, J = 2.2 Hz, 1H, Ph—H), 5.24 (d, J = 11.6 Hz, 1H, Piperidinyl-H), 4.57 (d, J = 5.2 Hz, 2H, —S—CH$_2$—), 4.43 (d, J = 11.9 Hz, 1H, Piperidinyl-H), 3.94 (t, J = 6.5 Hz, 2H, —O—CH$_2$CH$_2$CH$_2$CH$_2$—N—), 3.90 (s, 3H, Ph—OCH$_3$), 3.87 (s, 6H, Ph—OCH$_3$), 3.84 (s, 3H, Ph—OCH$_3$), 3.75 (s, 3H, Ph—OCH$_3$), 3.30-3.13 (m, 2H, Piperidinyl-H), 2.70-2.61 (m, 1H, Piperidinyl-H), 2.33 (t, J = 6.9 Hz, 2H, —O—CH$_2$CH$_2$CH$_2$CH$_2$—N—), 2.07 (s, 3H, N—CH$_3$), 1.79-1.70 (m, 2H, —O—CH$_2$CH$_2$CH$_2$CH$_2$—N—), 1.68-1.57 (m, 2H, —O—CH$_2$CH$_2$CH$_2$CH$_2$—N—), 1.49-1.40 (m, 2H, Piperidinyl-H), 1.39-1.28 (m, 2H, Piperidinyl-H). $^{13}$C NMR (101 MHz, DMSO) δ 193.20, 172.69, 164.19, 160.73, 158.62, 153.13, 151.97, 150.63, 149.80, 140.45, 139.80, 133.31, 126.13, 124.46, 108.92, 106.18, 96.37, 93.54, 72.09, 60.65, 59.67, 56.55, 56.52, 55.40, 52.99, 37.56, 37.10, 28.16, 27.87, 23.99. |

Test for Inhibition of Cancer Cell Activity by Compound of Embodiment 19 (Taking Hepatocellular Carcinoma SMMC-7721 Cells as an embodiment):

Testing Method (1) Cell Culture and Drug Effect

SMMC-7721 cells are cultured in DMEM high sugar medium containing 10% fetal bovine serum in a saturated humidity incubator at 37° C. and 5% CO2. The culture medium is changed every two days and passaged every 3-4 days. The drug is prepared as 1 mmol/L and 10 mmol/L storage solution using DMSO as solvent, when used, the concentration is diluted into 1 μmol/L and 10 μmol/L with culture medium, using DMSO as negative control group and gemcitabine as positive control group to act on cells in logarithmic growth phase.

(2) MTT Colorimetry

Cells in logarithmic growth phase are digested with 0.025% pancreatin, and then digested with DMEM high sugar medium containing 10% fetal bovine serum. After centrifugation, the cells are suspended in DMEM high sugar medium containing 10% fetal bovine serum. Take a 96-well plate and add 200 μL of sterile water seal to each hole around the plate to ensure saturated humidity in the experiment. In the middle six rows, 100 μL of cell suspension are added respectively, and the cell concentration is about 3.5×10$^4$ cells/mL. The last row is blank control group, and the same volume of complete culture medium is added. In 37° C., 5% CO2 saturated humidity incubator culture for 24 hours, cells completely adhere to the wall, remove the culture medium, add complete culture medium containing different drugs, 200 μL per hole. The blank control group is added with 200 μL of complete culture medium, and the culture is continued. After 24 hours, the drug effect is observed and photographed under an inverted microscope. After 48 hours, the drug effect is also observed and photographed under an inverted microscope. Then the supernatant is removed. 100 μL of 0.5 mg/mL MTT solution is added to each well. After 4 hours of continuous culture, purple crystal formazan is generated. 100 μL of 10% SDS is added to each well. After 12 hours of culture in an incubator at 37° C., the OD value is measured with an enzyme reader at A571 wavelength. Repeat 6 wells for each sample concentration, and calculate the inhibition rate by taking the average value.

$$\text{Inhibition rate (\%)} = \left(1 - \frac{OD \text{ value of drug treatment group}}{\text{Negative control group } OD \text{ value}}\right) \times 100\%$$

(3) Statistical Method

The experimental results are analyzed by SPSS11.5 and One-WayANOVA method, and $P<0.05$ showed that there are significant differences among the data.

2. Test Results of Inhibition of Hepatocellular Carcinoma SMMC-7721 Cell Activity

TABLE 3 in vitro inhibition rate of compound a prepared in Embodiments 1-18 on hepatoma SMMC-7721 cells for 48 hours at a set concentration

| Compound | Inhibition Rate (%) | |
|---|---|---|
| | 1 μmol/L | 10 μmol/L |
| A1 | 21.82 ± 2.34* | 95.51 ± 4.16* |
| A2 | 25.44 ± 3.25* | 96.13 ± 3.42* |
| A3 | 18.16 ± 2.14* | 97.35 ± 1.78* |
| A4 | 20.66 ± 1.21* | 99.85 ± 1.64* |
| A5 | 12.32 ± 2.39* | 97.52 ± 1.12* |
| A6 | 34.32 ± 2.69* | 98.12 ± 2.76* |
| A7 | 27.70 ± 1.09* | 99.35 ± 3.48* |
| A8 | 15.48 ± 2.74* | 99.85 ± 1.64* |
| A9 | 18.83 ± 3.15* | 99.76 ± 1.06* |
| A10 | 92.83 ± 3.84* | 97.85 ± 3.35* |
| A11 | 91.00 ± 2.86* | 99.85 ± 1.64* |
| A12 | 98.09 ± 2.68* | 99.28 ± 1.04* |
| A13 | 46.96 ± 4.65* | 99.76 ± 1.06* |
| A14 | 96.65 ± 2.61* | 100 ± 0.42* |
| A15 | 16.38 ± 3.82* | 99.52 ± 1.12* |
| A16 | 26.84 ± 4.36* | 99.85 ± 0.71* |
| A17 | 68.42 ± 2.35* | 100 ± 1.31* |
| A18 | 33.58 ± 1.67* | 100 ± 0.42* |
| Gencitabine | 55.67 ± 2.26* | 63.50 ± 2.18* |

Note: * the inhibitory rate of different drugs on SMMC-7721 cells at the set concentration is $P<0.05$ compared with the negative control group After preliminary tests, it is found that most of the compounds had no obvious inhibitory effect on SMMC-7721 cells at a concentration of 1 μmol/L, but showed significant inhibitory effect on SMMC-7721 cells at a concentration of 10 μmol/L, with the inhibitory rate exceeding 95%; The inhibition rate of some compounds to SMMC-7721 is over 90% at 1 μmol/L concentration or 10 μmol/L concentration, such as A10, A11, A12 and A14; The inhibitory activity is significantly higher than that of the positive control drug gemcitabine.

The above experimental activity data show that the dithiocarbamate-containing 4-(N-methyl) aminopiperidine myricetin derivative has a certain inhibitory effect on liver cancer SMMC-7721 cells, and some target compounds show excellent inhibitory activity on liver cancer SMMC-7721 cells, can be used as potential drugs for inhibiting liver cancer SMMC-7721 cells, and has a good application prospect.

As mentioned above, it is only a preferred embodiment of the present invention and is not intended to limit the present invention in any form. Any simple modifications, equivalent changes and modifications made to the above embodiments according to the technical essence of the present invention are still within the scope of the present invention.

The invention claimed is:

1. A 4-(N-methyl) aminopiperidine myricetin derivative containing dithiocarbamate, whose structural general formula is shown as follows:

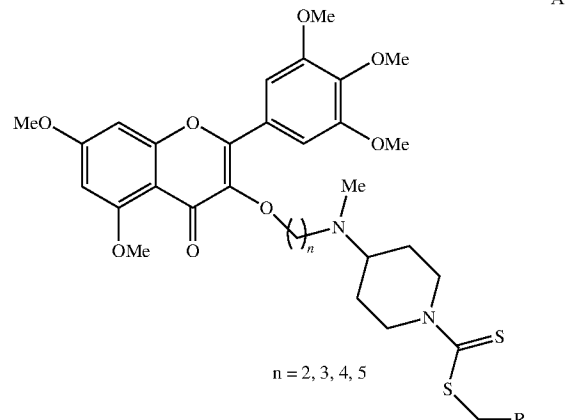

wherein R is substituted phenyl and substituted aromatic heterocyclic group; n is the number of carbon in the carbon chain and is 2, 3, 4 or 5.

2. The 4 (N-methyl) aminopiperidine myricetin derivative containing dithiocarbamate according to claim 1, wherein substituents on the substituted phenyl group are a C1-6 alkyl group, a C1-6 alkoxy group, a nitro group, a halogen atom or a hydrogen atom on the benzene ring.

3. The 4-(N-methyl) aminopiperidine myricetin derivative containing dithiocarbamate according to claim 1, wherein the aromatic heterocyclic group is selected from thienyl, furyl, pyrrolyl or pyridyl groups.

4. The 4 (N-methyl) aminopiperidine myricetin derivative containing dithiocarbamate according to claim 1, wherein the substituents on the substituted aromatic heterocyclic group are o-,m-, and p-C1-6 alkyl groups, C1-6 alkoxy groups, nitro groups, halogen atoms, or hydrogen atoms.

5. A preparation method of the 4-(N-methyl) aminopiperidine myricetin derivative containing dithiocarbamate according to claim 1 comprising the following specific steps:

(1) 3 hydroxy-3', 4', 5', 5, 7-pentamethoxymyricetin (an intermediate a) is prepared as follows:

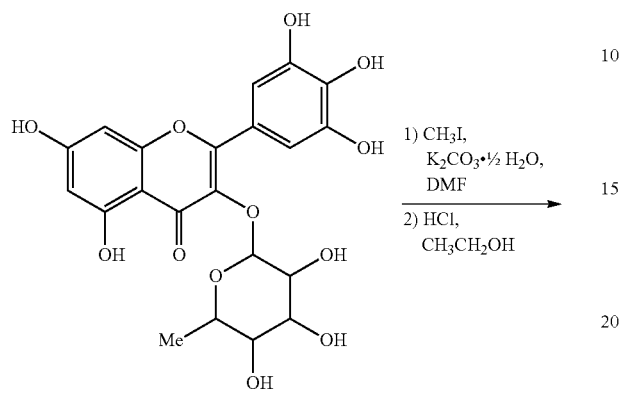

(2) 3-bromo-5,7-dimethoxy-2-(3,4,5-trimethoxyphenyl)-4H-chromene-4-one (an intermediate b) is prepared from the intermediate a and dibromoalkanes with different chain lengths using potassium carbonate as a catalyst and N,N-dimethylformamide (DMF) as a solvent as follows:

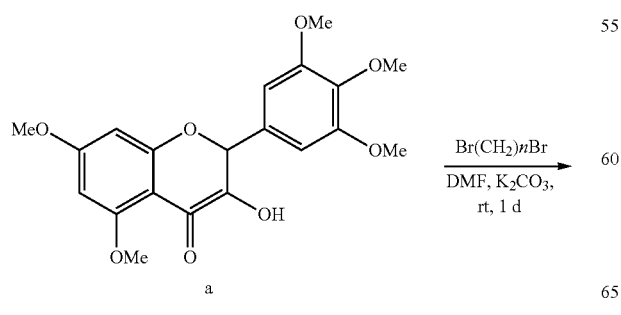

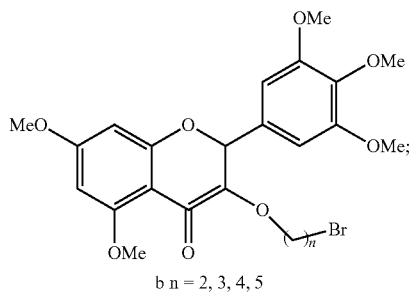

b n = 2, 3, 4, 5

(3) using the intermediate b and 4-(N-methyl)amino-N-Boc piperidine as raw materials, potassium carbonate as a catalyst and acetonitrile as a solvent, 3-(4-(N-methyl) amino-N-Boc piperidine)-5,7-dimethoxy-2-(3, 4,5-trimethoxyphenyl)-4H-chromene-4-one (an intermediate c) is prepared under reflux at 80° C. with continuous stirring, as shown below,

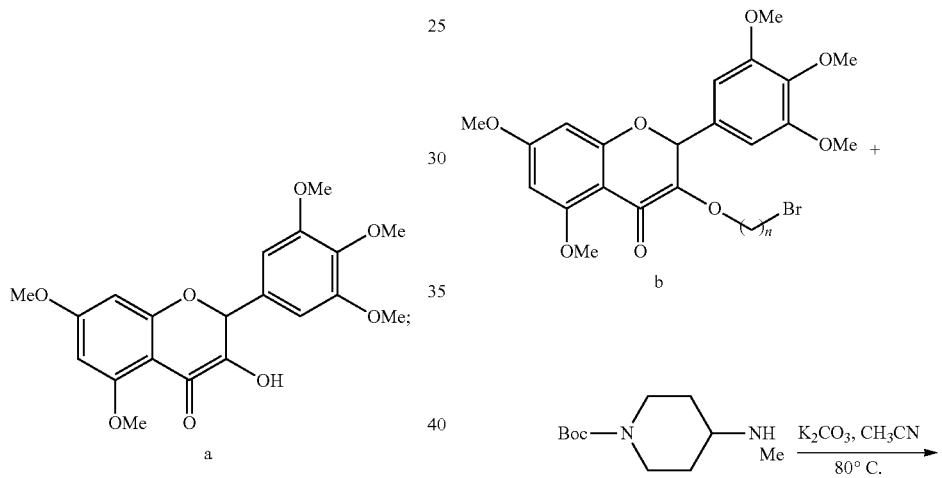

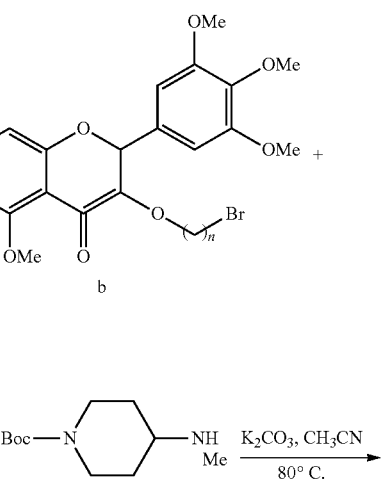

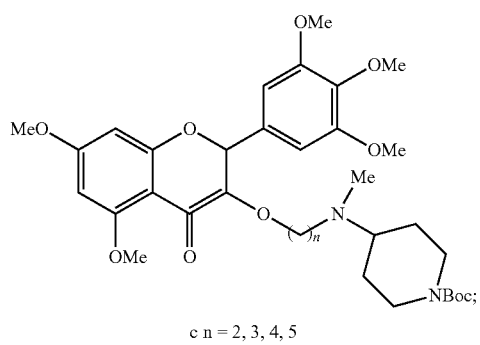

c n = 2, 3, 4, 5

(4) using the intermediate c as a raw material, a Boc protecting group is removed by hydrochloric acid acid (HCl) to obtain hydrochloride (an intermediate d) of 3-(4-(N-methyl) aminopiperidine)-5,7-dimethoxy-2-(3,4,5-trimethoxyphenyl)-4H-chromene-4-one, as shown below:

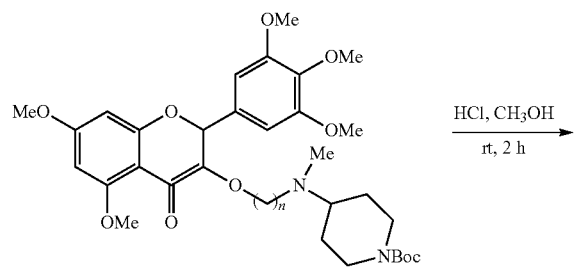
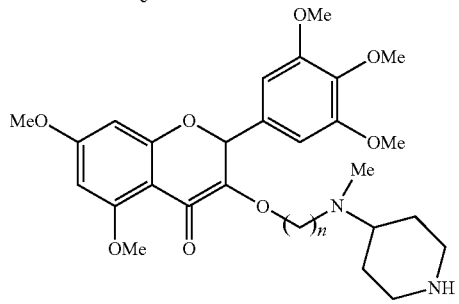
d n = 2, 3, 4, 5
(5) the 4-(N-methyl) aminopiperidine myricetin derivative containing dithiocarbamate (a target compound A) is prepared by using the intermediate d, carbon disulfide and benzyl chloride as raw materials, potassium carbonate as the catalyst and acetonitrile as the solvent, as shown below,
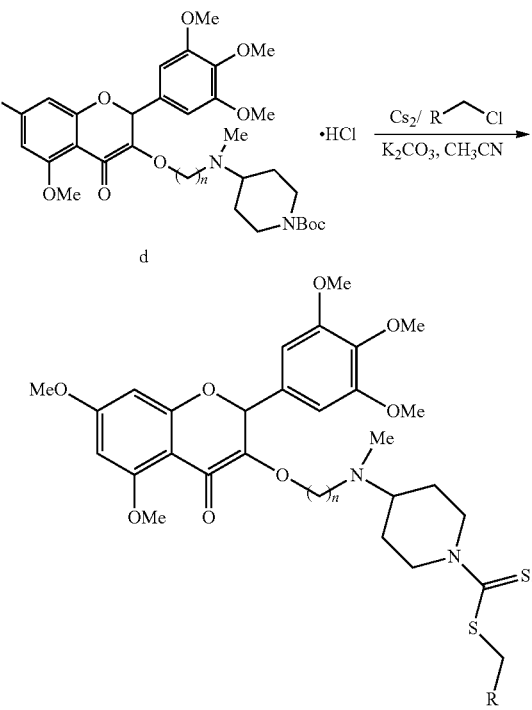
n = 2, 3, 4, 5 A
* * * * *